(12) United States Patent
Briskin et al.

(10) Patent No.: US 6,310,512 B1
(45) Date of Patent: Oct. 30, 2001

(54) INTEGRATED SELF-ADJUSTABLE CONTINUOUS TIME BAND PASS FILTER BASED UPON $G_M$ CELL WITH BIPOLAR TRANSISTORS

(75) Inventors: Boris Briskin, Vadnais Heights; William J. Linder, Golden Valley, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/447,176

(22) Filed: Nov. 22, 1999

(51) Int. Cl.$^7$ ................ H03K 5/00; G06G 7/12
(52) U.S. Cl. ............ 327/552; 327/362; 327/553; 327/103; 607/28
(58) Field of Search .................... 327/103, 552, 327/553, 560, 362; 330/305, 306, 256; 307/28

(56) References Cited

U.S. PATENT DOCUMENTS

| | | | |
|---|---|---|---|
| 4,596,251 | 6/1986 | Plicchi et al. | 607/20 |
| 4,686,987 | 8/1987 | Salo et al. | 600/24 |
| 4,823,797 | 4/1989 | Heinze et al. | 600/481 |
| 5,051,628 | 9/1991 | Hanna | 327/553 |
| 5,311,088 | 5/1994 | Nelson | 327/552 |
| 5,317,217 | 5/1994 | Rieger et al. | 307/521 |
| 5,391,190 | 2/1995 | Pederson et al. | 607/23 |
| 5,440,264 | 8/1995 | Sevenhans et al. | 327/553 |
| 5,578,064 | 11/1996 | Prutchi | 607/19 |
| 5,619,151 | * 4/1997 | Akioka et al. | 327/103 |
| 5,718,720 | 2/1998 | Prutchi et al. | 607/28 |
| 5,722,997 | 3/1998 | Nedungadi et al. | 607/28 |
| 5,726,600 | * 3/1998 | Raghavan et al. | 327/553 |
| 5,824,029 | 10/1998 | Weijand et al. | 607/122 |

* cited by examiner

*Primary Examiner*—Dinh T. Le
(74) *Attorney, Agent, or Firm*—Schwegman, Lundberg, Woessner & Kluth, P.A.

(57) ABSTRACT

An improved integrated self-adjustable continuous time band pass filter based upon a $G_m$ cell with $G_m$ compensation and bipolar transistors for use in a low power processing system for processing bursted amplitude modulated signals performing impedance-related measurements across a load. The system may be used for estimating stroke volume using the output and/or estimating hemodynamic maximum sensor rate using the output. The improved $G_m$ cell provides for stabilization of the transconductance by compensating for manufacturing process variation of the value of the linearizing resistance $R_G$ by varying the transconductance bias current using a feedback signal proportional to the resistance of a resistor which is a replicate of the linearizing resistor.

19 Claims, 8 Drawing Sheets

INTEGRATED SELF-ADJUSTABLE CONTINUOUS TIME BAND PASS FILTER BASED UPON $G_M$ CELL WITH BIPOLAR TRANSISTORS

FIELD OF THE INVENTION

This invention relates generally to an improved $G_m$ cell circuit useful for realizing a continuous time band pass filter and in particular to a method and apparatus for realizing a continuous band pass filter based upon a transconductance $G_m$ cell with bipolar transistors that is useful in an impedance sensor in biomedical applications.

BACKGROUND

The human body has electrical characteristics which can be measured for characterizing organ function and for the application of different therapies. For instance, the heart is a complex network of nerve and muscle tissue which operates in synchrony to pump blood throughout the body. Cardiac function may be monitored by sensing the electrical signals naturally conducted at certain places in the heart.

Sometimes it is convenient to apply signals to the body to determine the function of organs of the body. One way to apply signals is to use an implanted series of electrodes which apply a known current and measure the resulting voltage. The relationship between applied current and measured voltage is known as impedance. Thus, impedance is measured by injecting a known current using electrodes and monitoring the electrical voltage required to pass the known current between electrodes. The higher the magnitude of impedance, the higher the magnitude of voltage measured across the load for a known current magnitude.

If the electrodes are placed such that the impedance is measured across a right ventricular portion of the heart, then the impedance measured is a function of the stroke of the right ventricle. The stroke volume of the right ventricle provides a measure of the blood volume pumped by the heart into the lungs in one stroke.

The change in impedance is due to the conductive nature of blood and its changing volume in the left ventricle between contractions. The measured impedance will vary depending on the placement of the electrodes. For example, as shown in FIG. 1A and FIG. 1B, if a current is conducted between the housing of an implantable device 12 and a tip electrode 13 on the end of a catheter 14 with the tip electrode 13 positioned in the apex of the right ventricle 15, then the impedance observed between two electrodes, 16 and 17, located within the right ventricle (and before the tip electrode 13) will measure an increased impedance for a contracted ventricle (systole—FIG. 1B) as opposed to when the ventricle is not contracted (diastole—FIG. 1A). This is because in diastole, the ventricle is holding more blood and has more conductive volume to transfer current. In systole, the ventricle is contracted and has less blood, leaving less volume for conduction.

A system for indicating the stroke volume of the heart by tracking the impedance changes of the ventricle through contractions is shown in block diagram form in FIG. 2 through 4 of my commonly assigned copending patent application entitled System for Processing Bursted Amplitude Modulated Signals Using an Impedance Sensor, Ser. No. 09/297,004 filed Feb. 8, 1999. In that application there is shown a low power processing system for processing bursted amplitude modulated signals by performing impedance-related measurements across a load. The system operates by injecting current pulses of constant amplitude across the load using at least a first electrode and a second electrode, the current pulses including bursts of a plurality of pulses at a pulse frequency at which the current pulses are repeated, the bursts transmitted at a burst frequency. It includes detecting voltages across at least a third electrode and a fourth electrode; high pass filtering the voltages to produce filtered voltages; amplifying the filtered voltages to produce amplified voltage signals. It also includes bandpass filtering the amplified voltage signals with a bandpass filter with a center frequency equal to approximately the pulse frequency to generate first filtered signals; rectifying the first filtered signals to produce rectified signals; integrating the rectified signals to produce integrated signals; sampling-and-holding the integrated signals after each burst to capture an integrated pulse value for each burst, creating a plurality of discrete integrated pulse values. It also includes further bandpass filtering of the plurality of discrete integrated pulse values using a filter including an upper cutoff frequency less than the burst frequency to produce the output related to the time-varying impedance of the load.

In the system shown in my prior application referred to above, the realization approach used in the first bandpass filter 42 is continuous time filtering. Because the continuous time filter technique does not use a sampling clock, it is able to process a high frequency signal.

A potential disadvantage for utilization of this type of filter circuit may be the need for tuning circuitry. Tuning may be required because the filter coefficients are determined as a product of two dissimilar elements such as capacitors and resistors (or transconductors). Although the variation of values of capacitors in integrated circuits is small, in the order of ±5%, the variation in resistors may be ±50%. Another characteristic of continuous time filters is the presence of flicker noise and poor linearity. All of these characteristics are addressed by the present invention which provides an improved realization of a transconductance gain cell that is particularly adapted for use in a bandpass filter realized from a continuous time filter.

Thus there is a need in the art for a self-adjustable continuous time band pass filter with a transconductance cell having bipolar transistors and a self adjusting bias circuit to stabilize the overall transconductance of the transconductance cell.

SUMMARY OF THE INVENTION

Those skilled in the art, upon reading and understanding the present specification, will appreciate that the present self adjustable continuous time bandpass based upon an improved transconductance gain cell satisfies the aforementioned needs in the art and several other needs not expressly mentioned herein. An integrated gain-cell differential transconductor having an overall transconductance, $G_m$, is provided. The transconductor cell has a fixed transconductor portion coupled to a translinear gain cell. The fixed transconductor has at least one internal bias current I and is characterized by a transconductance determined by the reciprocal of the magnitude of a first linearizing resistor $R_{G1}$. The circuit also has a translinear gain cell operatively coupled to the output of the fixed transconductor and having at least one internal bias current $I_2$, the gain multiple of the translinear gain cell being determined by $I_2/I_1$ and the overall transconductance $G_m$ of the integrated gain-cell transconductor being $1/R_{G1} * I_2/I_1$. The circuit has variable bias current supply operatively coupled to the fixed transconductor which produces a bias control signal from a second resistor $R_{G2}$ which replicates $R_{G1}$ and varies bias current $I_1$ of the fixed transconductance portion in inverse proportion to the variation of $R_{G1}$, thereby compensating $G_m$ for variations in $R_{G1}$.

In one application, the fixed transconductor has a differential pair of input transistors and the linearizing resistor is comprised of a pair of resistors, each resistor having a resistance $R_{G1}/2$ which is connected in series with an emitter of each of the differential pair of input transistors of the fixed transconductor.

In another application the fixed transconductor has a differential pair of input transistors and the linearizing resistor has a resistance $R_{G1}$ and is connected between the emitters of the differential pair of input transistors of the fixed transconductor portion.

In one application a bandpass filter is realized using a plurality of transconductor gain cells, a plurality of capacitors connected to the outputs of at least some of the plurality of gain cells, and where the gain cells and the capacitors are connected for realizing a second order filter, wherein at least one of the transconductor gain stages is an integrated gain-cell differential transconductor having an overall transconductance, $G_m$, which is relatively unchanged by process variation. The transconductor including a fixed transconductor having at least one internal load current $I_1$ and characterized by a transconductance determined by the reciprocal of the magnitude of a linearizing resistance $R_{G1}$, a translinear gain cell operatively coupled to the output of the fixed transconductor and having at least one internal load current $I_2$, the gain multiple of the translinear gain cell being determined by $I_2/I_1$ and the overall transconductance $G_m$ of the integrated gain-cell transconductor being $1/R_{G1}*I_2/I_1$, and a variable bias circuit operatively coupled to the fixed transconductor to apply a bias current $I_1$ thereto, the magnitude of $I_1$ varying in inverse proportion to variations in the resistance of a resistor $R_{G2}$ which is a resistor formed to replicate $R_{G1}$, thereby compensating transconductance $G_m$ for variations in $R_{G1}$.

In another application an implantable medical device has an excitation source coupled to at least a first electrode and a second electrode, the excitation source producing current pulses of constant current flowing between the first electrode and the second electrode, the pulses sent in bursts at a burst frequency and having a pulse frequency at which the pulses are repeated, a first high pass filter filtering voltage signals received by at least a third electrode and a fourth electrode to produce filtered voltage signals. The device also has a first bandpass filter coupled to the amplifier and having a center frequency of approximately the pulse frequency; a rectifier coupled to the first bandpass filter and rectifying the filtered and amplified voltage signals to produce rectified signals and an integrator coupled to the rectifier and integrating the rectified signals to produce integrated signals, a sample-and-hold coupled to the integrator and sampling and holding the integrated signals to produce a plurality of samples; and a second bandpass filter coupled to the integrator and including an upper band cutoff frequency which is less than the burst frequency, the second bandpass filter filtering the plurality of samples to produce an output signal related to a time-varying impedance of a load and wherein the second bandpass filter has a plurality of transconductor gain cells, a plurality of capacitors connected to the outputs of at least some of the plurality of gain cells, and where the gain cells and the capacitors are connected for realizing the bandpass filter, wherein at least one of the transconductor gain stages is an integrated gain-cell differential transconductor having an overall transconductance, $G_m$, which is relatively unchanged by process variation, the differential transconductor having a fixed transconductor having at least one internal load current $I_1$ and characterized by a transconductance determined by the reciprocal of the magnitude of a linearizing resistance $R_{G1}$, a translinear gain cell operatively coupled to the output of the fixed transconductor and having at least one internal load current $I_2$, the gain multiple of the translinear gain cell being determined by $I_2/I_1$ and the overall transconductance $G_m$ of the integrated gain-cell transconductor being $1/R_{G1}*I_2/I_1$, and a variable bias circuit operatively coupled to the fixed transconductor to apply a bias current $I_1$ thereto, the magnitude of $I_1$ varying in inverse proportion to variations in the resistance of a resistor $R_{G2}$ which is a resistor formed to replicate $R_{G1}$, thereby compensating transconductance $G_m$ for variations in $R_{G1}$.

Other embodiments are provided and applications include the realization of other continuous time filters and implantable medical device circuits. Several embodiments are described in detail, however one skilled in the art upon reading and understanding the specification will appreciate that other embodiments exist and that the present description is not intended in a limiting or exclusive sense.

This summary is intended to be a general overview of the present system and is not intended in a limiting or exclusive sense. The invention described in the detailed description has a scope provided by the attached claims and their equivalents.

DETAILED DESCRIPTION

This detailed description provides a number of different embodiments of the present method and apparatus. The embodiments provided herein are not intended in an exclusive or limited sense, and variations may exist in organization, dimension, hardware, software, mechanical design and configuration, and chemical aspects without departing from the claimed invention, the scope of which is provided by the attached claims and equivalents thereof.

The present gain-cell transconductor signal processing system is demonstrated in the following detailed description in several embodiments. Some of the embodiments are gain cells used to realize continuous active filters for applications involving implantable devices, such as pacemakers and cardioverter-defibrillators, however, it is understood that the circuit may be used in any implantable device and may also be used by devices which are not implanted.

Figure 1B:
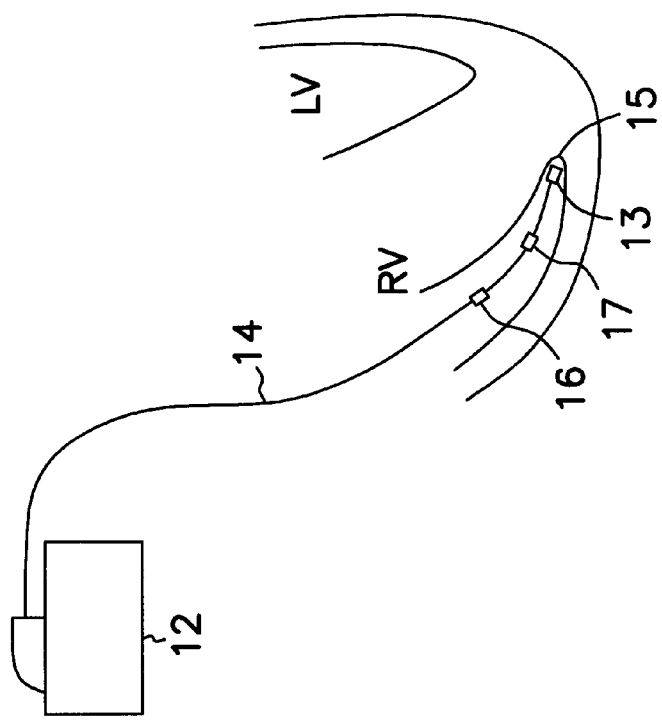
FIG. 1B is an example of an impedance measurement of a right ventricle of a heart in systole.
Figure 1A:
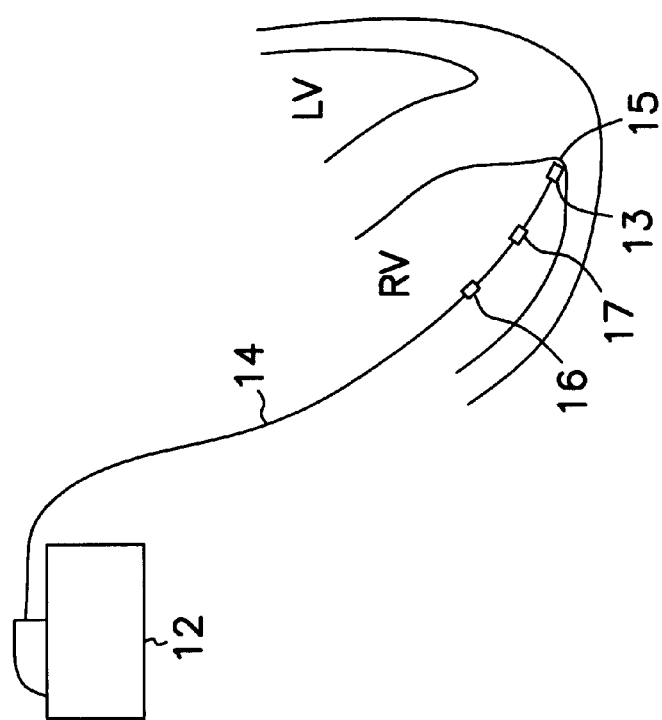
FIG. 1A is an example of an impedance measurement of a right ventricle of a heart in diastole.
Figure 2:
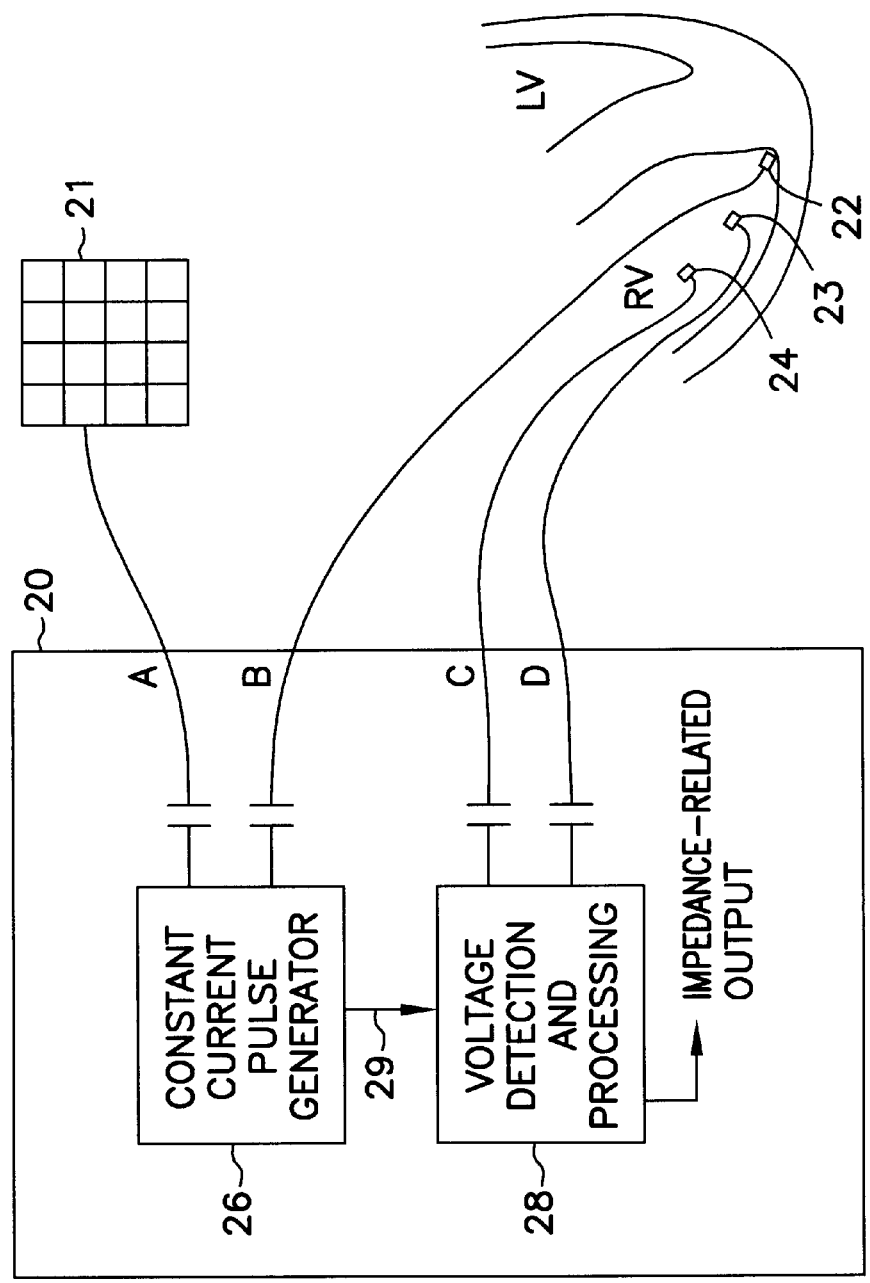
FIG. 2 is a block diagram showing a signal processing system according to one embodiment of the present system.

FIG. 2 is a block diagram showing a signal processing system according to one embodiment of the present system. Device 20 may be a pacemaker, cardioverter-defibrillator, or any other implantable device. Device 20 may also be located outside of the body. Electrodes 21 and 22 are located in the body in one embodiment. In one application electrode 21 may be an electrode external to the heart, including, but not limited to, a mesh, a catheter electrode, a patch electrode, or a conductive portion of the housing of an implantable device. If device 20 is an implantable device, then electrode 21 may be the conductive walls of the hermetically sealed device 20.

In one embodiment, electrode 22 is located near the apex of the right ventricle. Electrode 22 can be any type electrode, including, but not limited to, a tip electrode of a catheter electrode assembly.

In one embodiment, electrodes 21 and 22 are capacitively coupled to a constant current pulse generator 26. In one embodiment, the pulse generator 26 produces a number of different constant current waveforms. In one embodiment pulse generator 26 produces bursts of current pulses as shown in my prior application In this embodiment, these pulses are biphasic and are sent two at a time with a pulse frequency of 16 Khz and a burst frequency of 73 Hz. The pulses are constant current, which means that their 60 microamp peak-to-peak current value is regulated within 50 percent. In one embodiment, any current source design may be used to produce the constant current waveforms. Ideal constant current supplies have an infinite output impedance. In one embodiment the constant current source has a very large output impedance compared to the impedance load between the electrodes. In one embodiment the constant current source has an output which is greater than or equal to approximately 200 kiloohms. In embodiments where the electrodes are used to measure current across the cardiac area an output impedance of approximately 200 kiloohms was demonstrated to be adequate.

The waveform shown in my prior application is useful for measurements of right ventricular function, since the burst frequency is greater than twice the right ventricular frequency range of interest, as required by the Nyquist theorem. For example, the right ventricular frequency of interest lies between approximately 0.1 Hz and 25 Hz. Any burst frequency exceeding approximately twice the upper limit satisfies the Nyquist theorem. In this example, a burst frequency exceeding approximately 50 Hz is adequate. Additionally, the pulse frequency is much greater than the Nyquist frequency, providing smaller pulses for low energy consumption. Other waveforms may be generated by pulse generator 26 without departing from the present system.

In one embodiment, electrodes 23 and 24 are capacitively coupled to voltage detection and processing electronics 28. Processing electronics 28 produces an output related to the relative impedances of the tissue measured. The processing of signals received by electrodes 23 and 24 is based on the constant current pulses generated by pulse generator 26. In one embodiment, signal 29 is used to coordinate sensing events between pulse generator 26 and processing electronics 28. In embodiments involving active pacing or defibrillation of heart tissue, the signal 29 is used to inhibit sensing by processing electronics 28. In one embodiment, signal 29 is produced by a pacemaker, cardioverter-defibrillator, or other stimulator operating as part of or in conjunction with device 20. In one embodiment, processing electronics 28 are blanked during excitation of the cardiac tissue. In one embodiment involving pacing, the device 20 is used in an HMSR application to pace using the relative impedance of cardiac tissue to determine a maximal pacing rate for optimal hemodynamic function. In one embodiment, the device 20 is used in a minute ventilation measurement application.

Electrodes 23 and 24 may be any type of electrodes, including, but not limited to, catheter electrodes mounted on a common catheter with electrode 22 being a tip electrode. Thus, the constant current pulses from pulse generator 26 are transmitted between electrodes 21 and 22, which creates a voltage gradient across electrodes 23 and 24 which is related to the impedance of the electrical pathways between electrodes 21 and 22. As shown before, during diastole the impedance is less due to the larger conduction volume of the blood filling the ventricle than which is present in systole.

Figure 3:
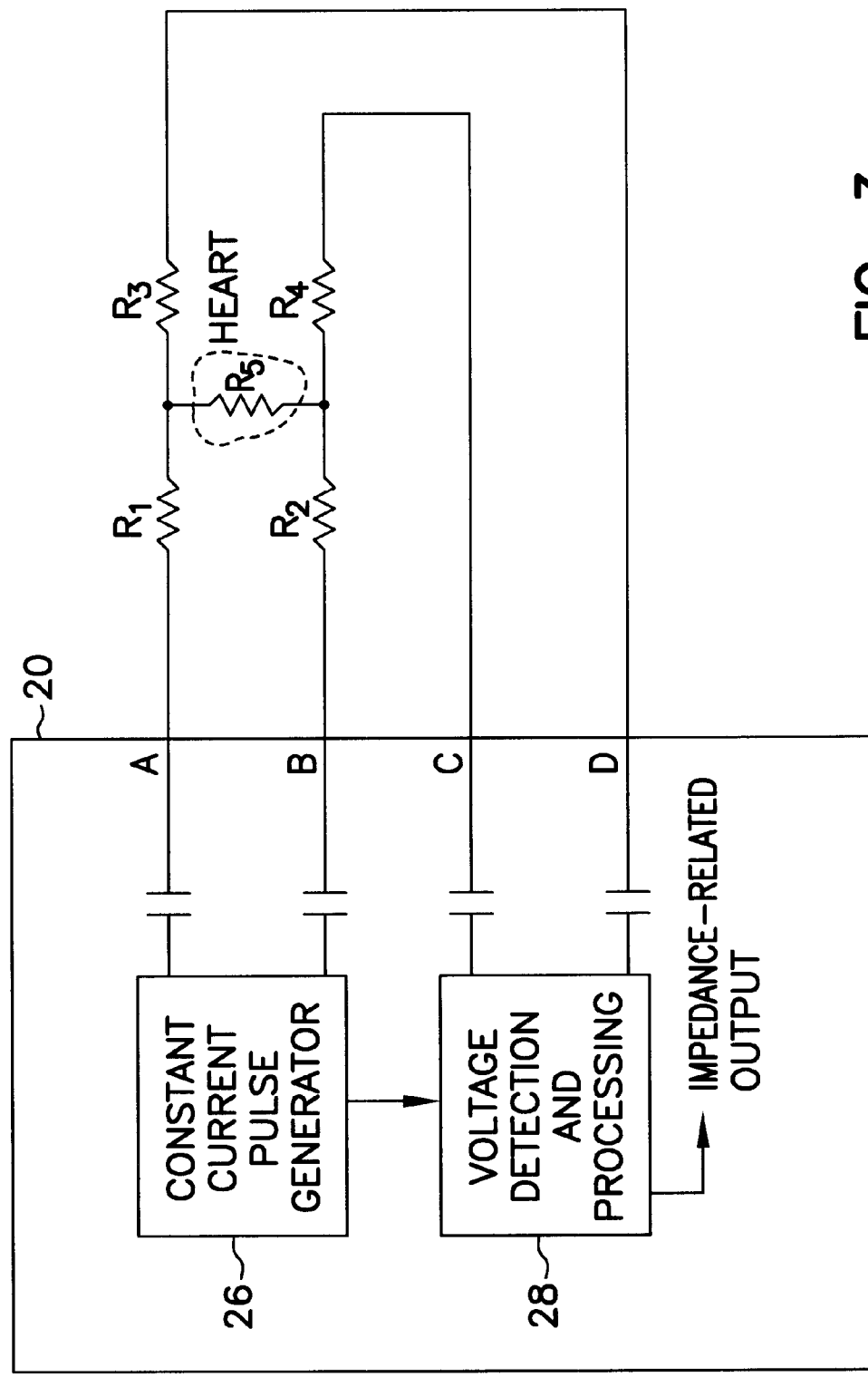
FIG. 3 is the block diagram of FIG. 2 where the heart and electrodes are modeled as impedances.

FIG. 3 relates to the block diagram of FIG. 2, except that the heart and electrodes are modeled as impedances. Impedances R1, R2, R3, and R4 are the impedances of the electrodes. Impedance R5 is the time-varying impedance of the heart's right ventricle.

Figure 4:
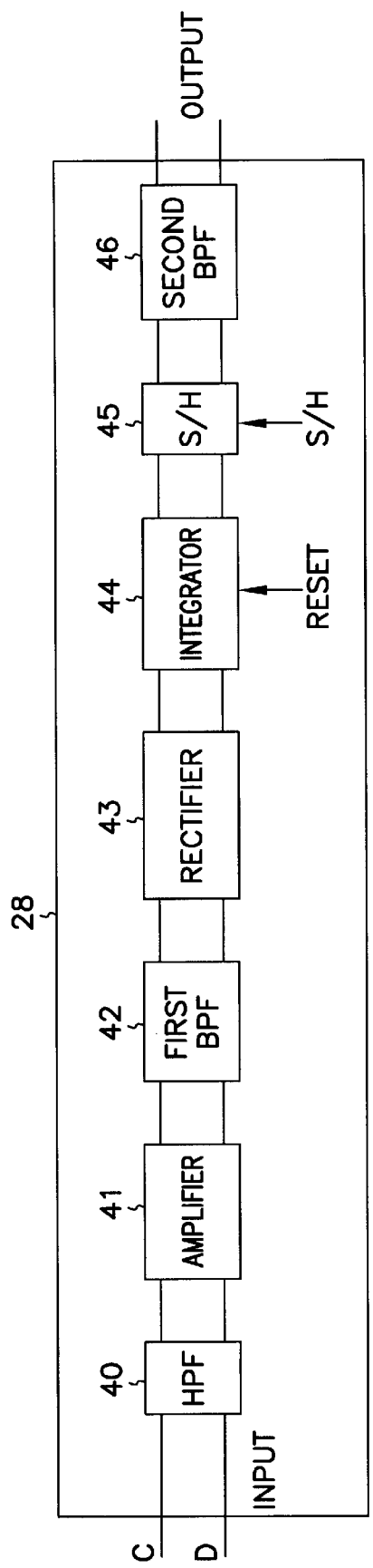
FIG. 4 is a block diagram of a signal processing system according to one embodiment of the present system.

FIG. 4 is a block diagram of voltage detection and processing electronics 28 according to one embodiment of the shown in my prior application. In this embodiment, pulse generator 26 (not shown in FIG. 4) provides constant current pulses. The resulting voltage signals are received by electrodes 23 and 24 and sent to inputs C and D of processing electronics 28 and to high pass filter 40. The high pass filter 40 has a low frequency cutoff of approximately 1000 Hz in one embodiment. The high pass filter 40 has a cutoff frequency above the spectral range of the r-waves produced by the heart in a cardiac application. In the embodiment with the cutoff of approximately 1000 Hz, the r-wave components are blocked by high pass filter 40, but the 16 Khz pulses are passed. Amplifier 41 amplifies voltage signals from high pass filter 40.

The amplified voltage signals are then bandpass filtered by first bandpass filter 42. The first bandpass filter 42 has a center frequency approximately equal to the carrier frequency of the constant current waveform, such as the pulse frequency in one embodiment of the present system. Such a filter removes spectral signals outside of the bandpass which are naturally generated as part of the square wave excitation signal and extracts substantially the fundamental frequency signal components, as is known from Fourier analysis of a square wave. The first bandpass filter selects a fundamental harmonic which is substantially sinusoidal and which may be processed by electronics tuned to the fundamental harmonic. In this way, the fundamental harmonic is the frequency of interest as it presents the best measure of signal-to-noise ratio.

The Q of the filter is adjusted to optimize this signal-to-noise ratio of the substantially fundamental harmonic components of the received signal. In one embodiment, the first bandpass filter has a center frequency of 16 Khz and a Q of 3. In one embodiment, depending on the Q of the bandpass filter 42, the number of peaks of the sine wave may exceed the number of current pulses per burst. Other embodiments provide different filter characteristics without departing from the present system. The first bandpass filter 42 is narrow enough to remove out of band extraneous noise which may have been amplified by amplifier 41.

The present invention relates to an integrated gain cell transconductor for use with an extended range input signal (1 v p/p) coming from the output of amplifier 41. Most integrated circuits presently manufactured use MOS semiconductors because of their ease of manufacture but the noise characteristics of those device have proved to be troublesome in many applications.

The use of bipolar transistors in the transconductor gain cell 60 allows for a reduction of noise in comparison to similar Gilbert cells using MOS transistors. Because of the unique bias circuit and bias control method shown in the disclosed embodiments, the gain performance of the transconductor 60 is less tied to manufacturing process limitations used to produce it than prior transconductor gain cells or Gilbert cells.

Gain cell transconductor 60 is particularly useful in an integrated analog filter such as band pass filter 42 of FIG. 4. When realized using the improved gain cell 60, band pass filter 42 does not require any special filter tuning mechanism and provides an output signal to rectifier 43 having an extended dynamic range which exhibits high linearity.

Figure 5:
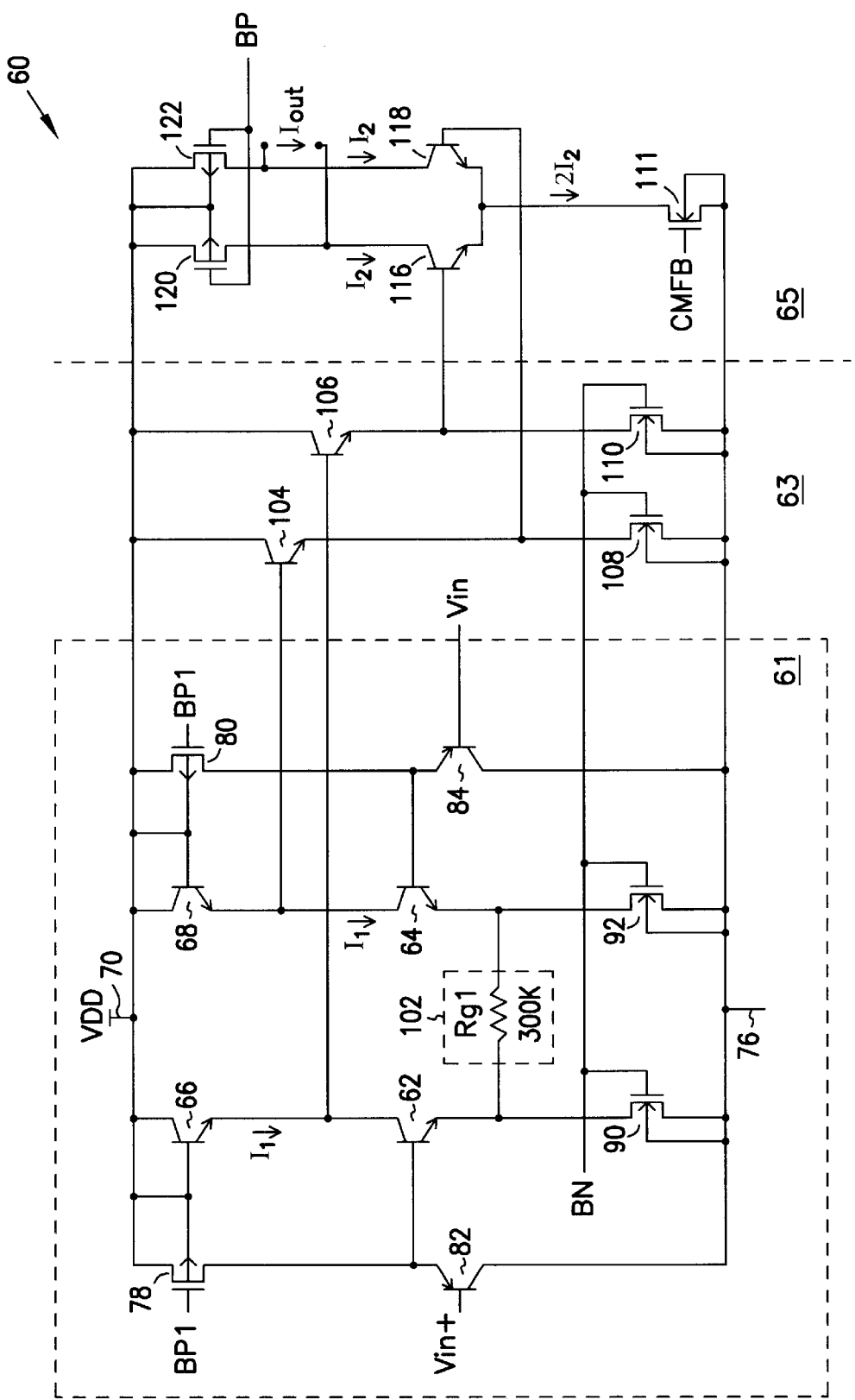
FIG. 5 is a schematic drawing of an embodiment of a Gain-cell transconductor with extended range for input signals.
Figure 7:
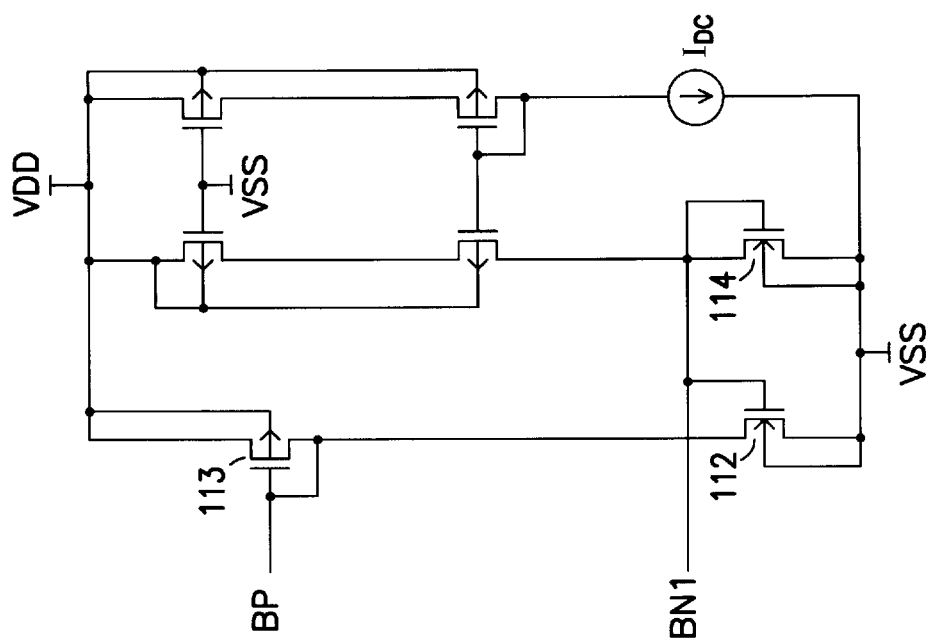
FIG. 7 is a schematic of an embodiment of a bias circuit for applying a fixed bias to the translinear gain cell portion of the gain cell transconductor.
Figure 6:
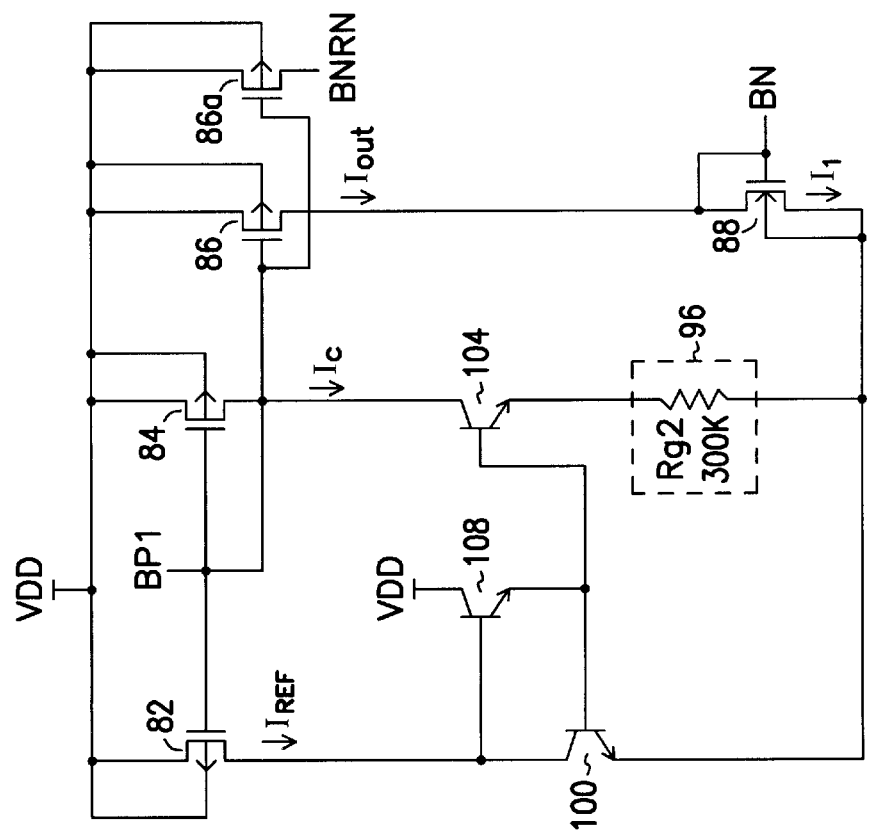
FIG. 6 is a schematic of an embodiment of a bias circuit for applying a control signal to the fixed transconductor portion of the gain cell transconductor.

A portion of an embodiment of a gain-cell transconductor 60 is illustrated in the schematic diagram of FIG. 5. The circuitry is divided for explanatory purposes into a fixed transconductor portion 61, a level shifter portion 63 and a translinear gain cell portion 65. The variable and fixed bias circuits providing bias signals to gain-cell transconductor 60 are shown in FIGS. 6 and 7 respectively.

Fixed Transconductor Portion

Referring first to the fixed transconductor cell portion 61, it can be seen that the circuit comprises matched bipolar NPN transistors 62 and 64 which are connected as a differential pair. The collectors of each transistor 62, 64 are in turn connected to the emitters of NPN transistors 66, 68, the collectors of which are connected to power supply or positive bus 70. Since the bases of transistors 66 and 68 are both directly tied to positive bus 70, those transistors 66 and 68 act as forward biased PN junctions which deliver currents $I_1$ to both sides of the differential transistor pair 62, 64.

A bias signal BP1, derived from the variable bias current circuit of FIG. 6, as discussed later below, is connected to the gate terminals of CMOS transistors 78 and 80. The source terminals of transistors 78 and 80 are both connected to the power supply 70 so that those transistors supply a controlled current to the emitters of transistors 82 and 84 in accordance with the signal at BP1.

A bias signal BN, also derived from the variable bias current circuit of FIG. 6, is connected to the gates of CMOS 90 and 92. The source terminals of CMOS 90 and 92 are both connected to the emitters of transistors 62 and 64.

Turning now to the bias circuit in FIG. 6, it can be seen that p channel CMOS transistors 82 and 86 form a "current mirror" with p-channel CMOS transistor 84 which has its gate terminal connected to its drain terminal so that it is "diode connected".

Returning now to FIG. 5, the bases of transistors 62 and 64 are connected respectively to the emitters of PNP input stage transistors 82, 84 the collectors of which are connected to ground 76. Transistors 82 and 84 are connected as emitter followers with p channel CMOS transistors 78 and 80 connected between their emitters and the power supply 70. Thus a input signal $V_{in}$ applied to the bases of transistors 82 and 84 is essentially transferred to the bases of the differential transistor pair 62, 64. Assuming that the base emitter voltage drop is essentially equal for each of the transistors 62 and 64, the input signal $V_{in}$ will appear across linearizing resistor 102 which has a nominal resistance $R_{G1}$ and is connected between the emitters of the transistors 62, 64.

If we then designate $i_{o1}$ as the difference between the collector currents of transistors 62 and 64 for a given input signal $V_{in}$, it can be seen that $$i_{o1}=V_{in}/R_{G1}$$

In other words, the transconductance of the fixed transconductor stage 61 is determined by $1R/_{G1}$. Because resistors, such as $R_{G1}$, which are formed in integrated circuits have a large variation in resistance caused by normal process variations in the integrated circuit manufacturing process, it can be seen that having the transconductance determined by the $R_{G1}$ value of linearizing resistor 102 may lead to large variations in transconductance between different circuits. This sensitivity of the tranconductance to the magnitude of $R_{G1}$ is a major drawback of conventional transconductor gain devices which is minimized or avoided in devices in accordance with bias compensation in accordance with the present invention.

The sensitivity of the transconductance to the magnitude of $R_{G1}$ in one embodiment is compensated for by the variable bias current supply circuit of FIG. 6. In FIG. 6 it can be seen that resistor 96 has a resistance $R_{G2}$ where the positioning of resistors 96 and 102 on the substrate on which the circuit is realized is determined so that $R_{G1}$ is closely matched to $R_{G2}$ and their values are substantially equal for any particular circuit although manufacturing process variations allow them both to vary substantially from circuit to circuit without varying from each other. In actual practice the individual resistors comprising $R_{G1}$ and the actual resistors that comprise $R_{G2}$ are laid out on the substrate upon which the circuitry is realized so that the individual resistors are closely adjacent to each other and also laid out so that the resistors comprising $R_{G1}$ and those comprising $R_{G2}$ are intermediate each other. This matching of the manufacturing processes and the selection of intermediately adjacent locations of resistors 96 and 102 on the substrate is referred to herein as making them "replicates of each other". In other words, resistor 96 is a replicate of resistor 102.

In order to reduce distortion it is important to set the value of $R_G$ high enough so that it is much higher than the maximum small signal emitter resistance $r_{emax}$ of transistors 62 and 64. In order to optimize the linearity of the circuit, it is necessary to keep the bias currents $I_1$ large (to keep $r_e$ small) and the input signal should be small (to maintain the small values of $r_e$). However, a practical limit on the reduction of the magnitude of the input signals is the possibility of noise becoming a problem.

In order to reduce the variability of the transconductance of the fixed transconductor 61 based upon variations in $R_G$, a variable bias supply arrangement with feedback from a resistor which is a replicate of the linearizing resistor has been devised. Transistors 90 and 92 have their drain terminals connected to the emitter terminals of the differential pair of transistors 62 and 64 and serve as bias current generators for those transistors based upon the signal applied to node BN by the bias generation circuitry of FIG. 6.

It can also be seen that p channel CMOS transistors 82 and 86 form a "current mirror" with p-channel CMOS transistor 84 which has its gate terminal connected to its drain terminal so that it is "diode connected". At room temperature, the current sourced by transistor 84 is approximately 60 nanoamperes. CMOS transistors 82, 84 and 86 operate as current mirrors which each supply a current proportional to absolute temperature (PTAT) that is also proportional to the PTAT current provided by diode connected CMOS 84. In one embodiment CMOS transistors 82, 84 and 86 all have similarly matched dimensions and characteristics such that their currents are all substantially equal. In other embodiments it may be appropriate to scale the semiconductor geometry differently so as to produce currents that are scaled relative to each other.

It is further shown in FIG. 6 that the connection of the drain to the gate terminal of transistor 88 makes it "diode connected". The connection of gate, node BN, to the gates of transistors 90 and 92 of FIG. 5 causes each of them to operate as current mirrors driving currents $I_1$, which are proportional to the PTAT current passing through transistor 88. N-channel transistor 88 provides a temperature compensated current sink for the current drawn by transistor 86. The current from the bias current generator of transistor 82 forward biases the base emitter junction of NPN transistor 108 and the base emitter junction of NPN transistor 100, and establishes a proportional to absolute temperature (PTAT) voltage at the base of transistor 104 which is in turn applied across resistor 96.

The signal voltage at the collector of transistor 104 increases with increases in $R_{G2}$ thereby raising the voltage at the gate of CMOS transistor 86, reducing the current flow, and thereby causing the bias voltage at node BN to drop and to reduce the bias current $I_1$ through CMOS transistors 90 and 92. Thus bias current generators 90 and 92 drive a bias current $I_1$ which is inversely proportional to changes in $R_G$.

Translinear Gain Cell Portion

The differential output current $i_{o1}$ from the fixed transconductor stage 61 is connected to the bases of NPN transistors 104 and 106 which have active emitter loads comprised respectively of current mirror n-channel CMOS 108 and 110. Transistors 104 and 106 act as level shifters 63 coupling the transconductance portion 61 to the gain cell portion 65. The current for CMOS 108 and 110 is proportional to the current drawn by n channel CMOS 88, shown in FIG. 6.

The output of the level shifter portion 63 of the circuit is taken from the emitters of transistors 104 and 106 which are connected to the base terminals of a differential pair of transistors 116, 118 of translinear gain cell portion 65. The common emitters of transistors 116 and 118 are biased by the current established by current mirroring CMOS 120 and 122. The respective collectors of load transistors 116 and 118 are biased by p mode CMOS 120 and 122 which are biased by the signal at node BP which is at the drain of current mirror FET 113 in the bias circuit of FIG. 7.

When no differential input voltage is applied to transistors 116 and 118, their collector currents are maintained at a bias current I2. The differential output current, $I_{out}$, of the translinear gain cell 65 is taken from the collectors of the pair of differential transistors 116 and 118.

The overall transconductance of the fixed transconductor gain cell combination 60 can be shown to be the following:

$$Gm = \frac{1 \times I_2}{R_{G1} \times I_1}$$

When the Gain-cell transconductor 60 is realized in an integrated circuit, it is well known that the manufacture of such circuits is subject to considerable process variations in the realization of certain parameters, most especially of the resistance of $R_{G1}$ since variations in the resistance of integrated circuit resistors may be as large as ±50% between otherwise satisfactory circuits. Since the trans-conductance of the overall circuit is proportional to $1/R_{G1}$, in order to hold $G_m$ relatively constant, it is necessary to modify the ratio of the bias currents $I_2$ to $I_1$ in such a manner as to offset the anticipated variations in $R_{G1}$ between circuits.

As shown above, the bias circuit of FIG. 6 operates to provide a variable bias current $I_1$ for the transconductor stage 61 so as to hold $G_m$, the transconductance of the overall circuit at the nominal point despite the existence of manufacturing process variations between circuits which may exceed ±50%.

Stabilization of $G_m$ for variations in $R_{G1}$ is done by using a replicate resistor 96, having a resistance $R_{G2}$ as a feedback resistor in the variable bias circuit to alter the bias current of the fixed transconductor portion 61 so that the product of the ratio $I_2/I_1$ with the reciprocal of $R_{G1}$ remains essentially constant, despite variations in $R_{G1}$ introduced by manufacturing process variation between circuit chips. Because resistors 96 and 102 are manufactured during the same process run on the same substrate and therefore are replicates of each other, the magnitude difference between the resistor 102 in the transconductor 61 and in resistor 96 in the bias circuit are relatively small, and $I_1$ is therefor forced to vary in inverse proportionality to the variations of Rg of resistor 102 from nominal.

Universal Filter Based Upon the Improved Gain Cell

Figure 8:
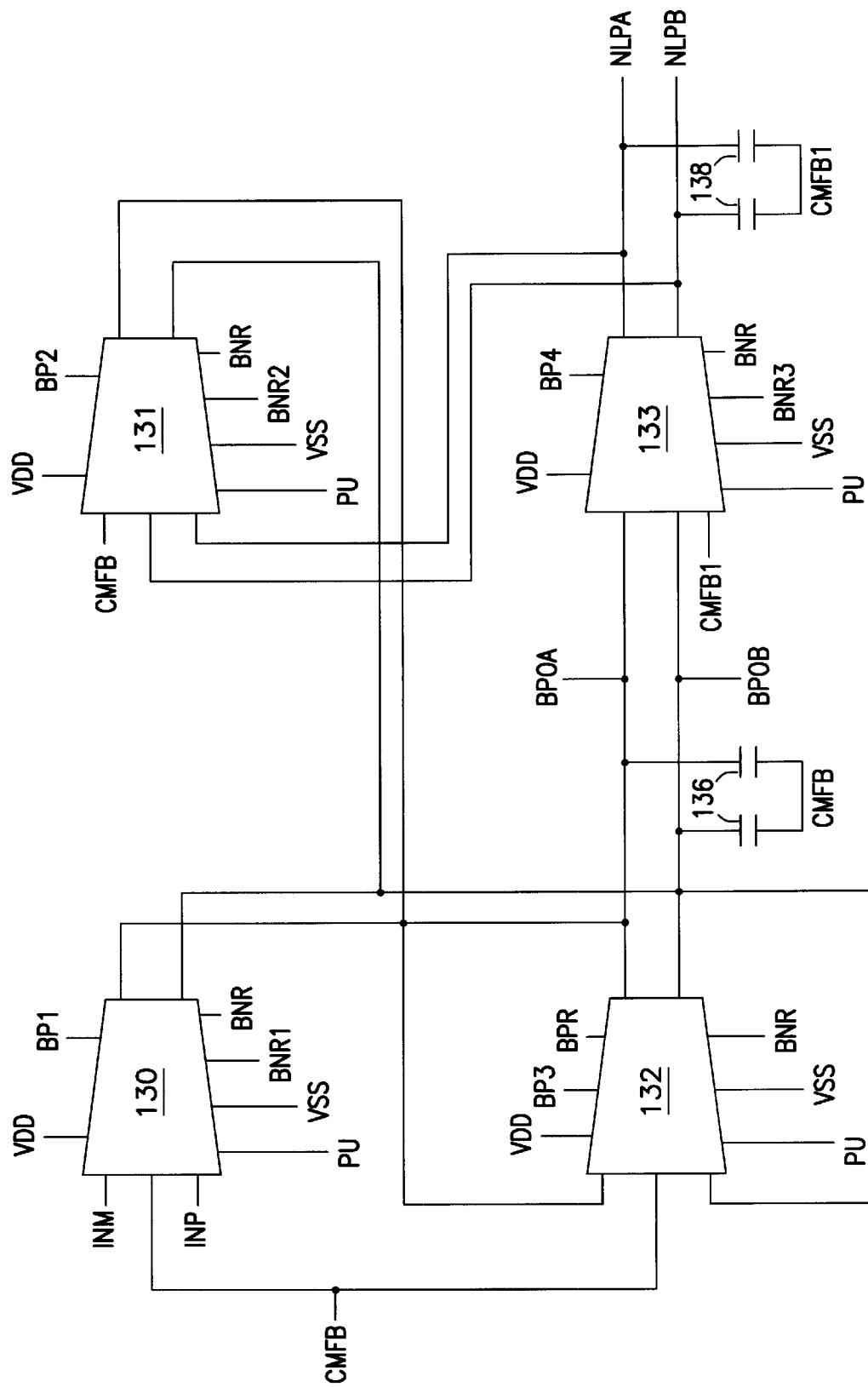
FIG. 8 is a schematic of an embodiment of a universal filter utilizing the Gain cell transconductor according to the present invention.

FIG. 8 illustrates, in generalized block diagram form, a band pass filter mechanized with the improved gain cell according to the present invention. In one embodiment, it may correspond to the first bandpass filter 42 of FIG. 4. The differential input signal from the preceding amplifier 41 is applied to the terminals designated INM and INP of gain cell 130. The bandpass output differential signal is produced at the terminals BPOA and BPOB and, in the system illustrated in FIG. 4 may be connected to the input of rectifier 43. As can be readily appreciated, the improved transconductance gain cell disclosed herein can also find suitable use in active continuous filters other than bandpass filters. Such filters may include second-order or biquad filters such as notch filters, high pass and low pass filters and variants thereof.

Figure 9:
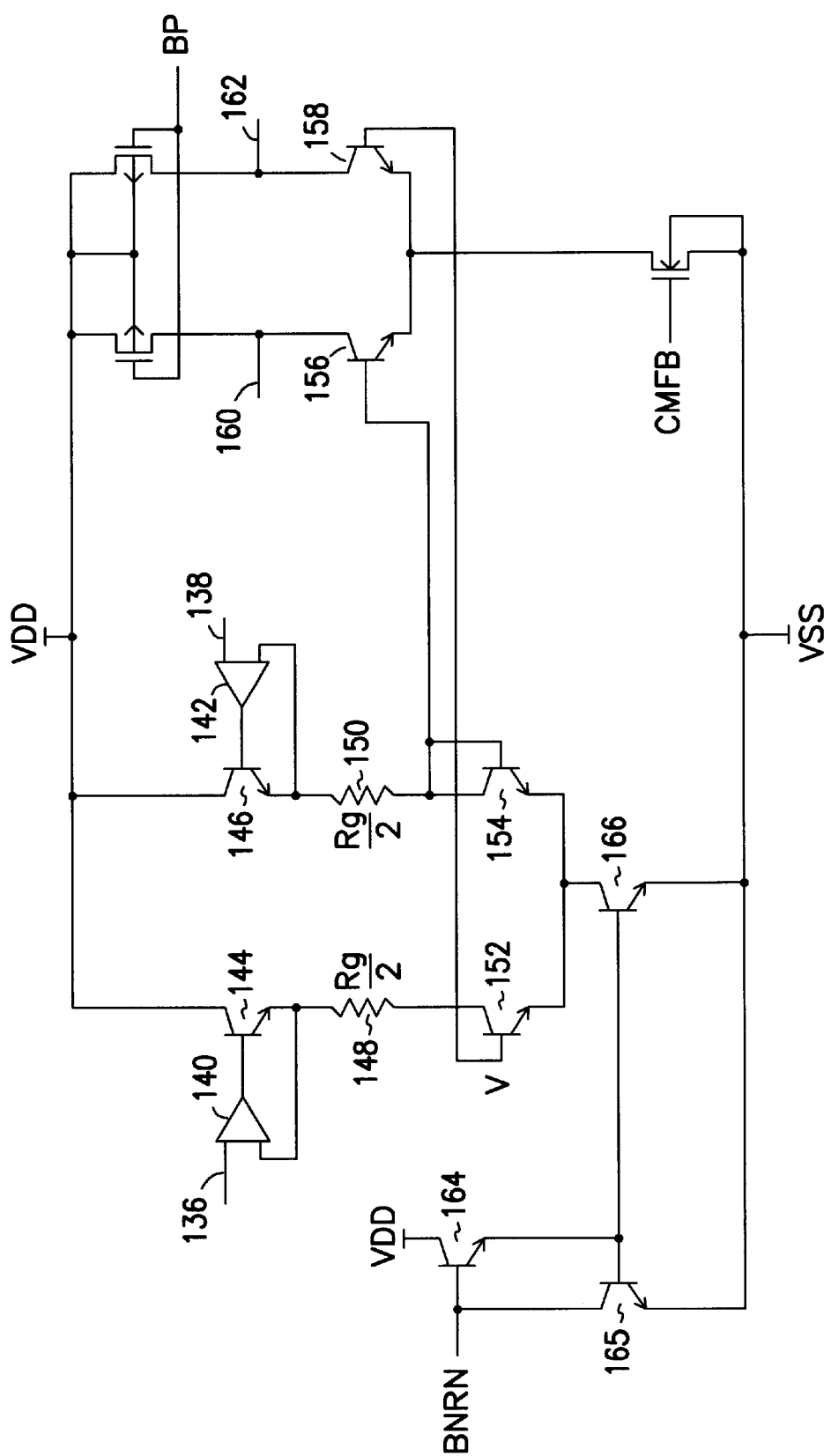
FIG. 9 is a schematic of another embodiment of a gain cell transconductor.

The bandpass filter of FIG. 8 utilizes four transconductor gain cells 130, 131, 132 and 133. In the embodiment shown, one of the cells 132 may correspond to the cell 60 as illustrated in FIGS. 5 through 7. In one embodiment the other three gain cells 130, 131 and 133 may correspond to another embodiment of the gain cell having circuitry as shown in FIG. 9. All of the cells 130, 131, 132 and 133 utilize the bias compensation circuitry of FIG. 6 to compensate for manufacturing variations of the linearizing resistors whether the resistance is connected across the emitters of the differential input transistor pairs as in FIG. 5, or as separate resistances of $R_G/2$ in series with the emitters of the differential input transistor pair as in FIG. 9 which is described in detail below.

The basic arrangement of the bandpass filter circuit corresponds generally to functional component arrangements that are known in the art for realizing continuous filters using Gilbert cells, with the primary exception and improvement being the use of the bias feedback circuit of FIG. 6 which is used to generate each of the compensated bias control signals for transconductance gain cells 130, 131, 132 and 133. The "fixed" bias control signals are generated by a fixed bias circuit which may correspond to the circuit shown in FIG. 7. Suitable circuitry for providing for common mode feedback CMFB is also provided but not shown in detail since it is well known and not a part of the present invention.

In FIG. 8, the pairs of capacitors 136, and 138 cooperate with the transconductance of two of the cells 132 and 133 to provide the second order break points of the filter. In one embodiment where the band pass filter 42 of FIG. 4 has a center frequency of 16 kHz, the capacitors may each have a typical capacitance of about 22 pf.

The gain cell transconductor circuit of FIG. 9 illustrates the use of another embodiment or variation of a gain cell that serves to reduce the distortion properties of the fixed transconductor 61 without using large bias currents and small input signal levels. As shown, the input terminals 136 and 138 to the gain cell are initially connected to the inputs to a pair of differential amplifier stages 140 and 142 which, in turn, drive the bases of the differential pair of input transistors 144, 146. The emitters of transistors 144, and 146 are each connected through linearizing resistors 148, and 150 to the collectors of transistors 152 and 154 which are diode connected. Each of the resistors 148 and 150 has a resistance $R_g/2$ which is replicated in resistor 96 of the bias circuit of FIG. 7.

The virtual ground provided in each of the op amps 140 and 142 forces the emitter voltages of transistors 144 and 146 to be equal to input signals $v_{1+}$ and $v_{1-}$. As a result, the input voltage signal appears directly across resistors 148 and 150 and does not depend upon the base emitter voltage drops of transistors 144 and 146. The remainder of the circuitry of FIG. 9 is generally similar to that discussed in connection with FIG. 5.

The signals from the collectors of transistors 152 and 154 are connected to the bases of transistors 156 and 158 and the outputs for the circuit are taken at terminals 160 and 162 of the gain stage. Transistors 164, 165 and 166 and the CMOS shown are all used to set the various bias currents for the transconductance and gain stages. The compensated bias command is connected to the base of transistor 164 as shown to set the compensated bias current for the input differential pair of transistors 144 and 146.

The present signal processing system based upon the improved transconductance gain cell may be incorporated or used in combination with a variety of devices and applications, including, but not limited to, the devices and applications described in detail by the documents incorporated by reference in this patent application. Other devices and applications incorporating the present teachings will be readily apparent to those skilled in the art upon reading and understanding the present detailed description.

What is claimed:

1. An integrated gain-cell differential transconductor having an overall transconductance, $G_m$, comprising:
    a fixed transconductor having at least one internal bias current $I_1$ and characterized by a transconductance determined by a reciprocal of the magnitude of a first linearizing resistor $R_{G1}$;
    a translinear gain cell operatively coupled to an output of the fixed transconductor and having at least one internal bias current $I_2$, a gain multiple of the translinear gain cell being determined by $I_2/I_1$ and the overall transconductance $G_m$ of the integrated gain-cell transconductor being $1/R_{G1} \cdot I_2/I_1$; and
    a variable bias current supply operatively coupled to the fixed transconductor and producing a bias control signal from a second resistor $R_{G2}$ which replicates $R_{G1}$ and varies the internal bias current $I_1$ of the fixed transconductor in inverse proportion to the variation of $R_{G1}$, thereby compensating $G_m$ for variations in $R_{G1}$.

2. The differential transconductor of claim 1 wherein the fixed transconductor has a differential pair of input transistors and the linearizing resistor is comprised of a pair of resistors, each resistor having a resistance $R_{G1}/2$ which is connected in series with an emitter of each of the differential pair of input transistors of the fixed transconductor.

3. The differential transconductor of claim 1 wherein the fixed transconductor has a differential pair of input transistors and the linearizing resistor has a resistance $R_{G1}$ and is connected between the emitters of the differential pair of input transistors of the fixed transconductor portion.

4. A differential gain cell transconductor having a transconductor portion, a translinear gain cell portion and a dynamic bias circuit, said transconductor comprising;
    a pair of differentially connected transconductor input transistors connected to receive a differential transconductor input voltage signal $V_i$ at a pair of input terminals thereof and producing a transconductor output voltage, the transconductor portion having a linearizing resistance $R_{G1}$ operatively associated therewith such that the transconductance of the transconductor is $1/R_{G1}$ and also having an internal bias current $I_1$;
    a translinear gain cell portion having input terminals and output terminals and an internal bias current output $I_2$, the gain cell portion having a gain which is proportional to $I_2/I_1$;
    a circuit connected between the output terminals of the pair of transconductor input transistors and the input terminals of the translinear gain cell portion; and
    a dynamic bias circuit having a bias resistor having a resistance $R_{G2}$ associated therewith which is a replicate of $R_{G1}$, said bias circuit providing bias currents $I_1$ to the pair of transconductor input transistors, the magnitude of current $I_1$ having a magnitude which varies in inverse proportion to variations in the resistance of $R_{G2}$ thereby compensating the transconductance gain of the differential cell transducer for variations in $R_{G1}$.

5. The gain cell transconductor of claim 4 wherein the transistors are bipolar transistors.

6. The gain cell transconductor of claim 5 wherein the input terminals of the pair of transconductor input transistors are base terminals.

7. The gain cell transconductor of claim 5 wherein the output terminals of the pair of transconductor input terminals collector terminals.

8. The gain cell transconductor of claim 6 wherein the linearizing resistance is connected between the emitters of the transconductor input transistors.

9. The gain cell transconductor of claim 8 wherein the linearizing resistance is a single resistor having a resistance Rg.

10. The gain cell transconductor of claim 6 wherein the linearizing resistance is made up of a pair of resistors, each having a resistance Rg/2 and each connected to an emitter of one of the pair of transconductor input transistors.

11. An integrated gain-cell differential transconductor having an overall transconductance, $G_m$, comprising:
    a fixed transconductor having a pair of internal bias currents $I_1$ and characterized by a transconductance determined by the reciprocal of the magnitude of a first linearizing resistor, $R_{G1}$;
    a translinear gain cell operatively coupled to the output of the fixed transconductor and having at least one internal bias current $I_2$, the gain multiple of the translinear gain cell being determined by $I_2/I_1$ and the overall transconductance $G_m$ of the integrated gain-cell transconductor is $1/R_{G1} \cdot I_2/I_1$; and
    variable bias current supply means operatively coupled to the fixed transconductor by producing a control signal from a feedback resistor $R_{G2}$, having resistance characteristics which replicate $R_{G1}$, the control signal being operative for varying the bias current $I_1$ of the fixed transconductor in inverse proportion to the variation of $R_{G1}$ thereby compensating $G_m$ for variations in $R_{G1}$.

12. In a bandpass filter having a plurality of transconductor gain cells, a plurality of capacitors connected to the outputs of at least some of the plurality of gain cells, and where the gain cells and the capacitors are connected for realizing a second order filter, wherein at least one of the transconductor gain stages is an integrated gain-cell differential transconductor having an overall transconductance, $G_m$, which is relatively unchanged by process variation, comprising:

a fixed transconductor having at least one internal load current $I_1$ and characterized by a transconductance determined by the reciprocal of the magnitude of a linearizing resistance $R_{G1}$;

a translinear gain cell operatively coupled to the output of the fixed transconductor and having at least one internal load current $I_2$, the gain multiple of the translinear gain cell being determined by $I_2/I_1$ and the overall transconductance $G_m$ of the integrated gain-cell transconductor being $1/R_{G1}*I_2/I_1$; and a variable bias circuit operatively coupled to the fixed transconductor to apply a bias current $I_1$ thereto, the magnitude of $I_1$ varying in inverse proportion to variations in the resistance of a resistor $R_{G2}$ which is a resistor formed to replicate $R_{G1}$, thereby compensating transconductance $G_m$ for variations in $R_{G1}$.

13. The bandpass filter of claim 12 wherein linearizing resistance $R_{G1}$ is comprised of a pair of resistors having resistance $R_{G1}/2$.

14. The bandpass filter of claim 12 wherein linearizing resistance $R_{G1}$ is comprised of a single resistor.

15. A continuous active filter comprised of a plurality of transconductor gain cells, a plurality of capacitors connected to the outputs of at least some of the plurality of gain cells, and where the gain cells and the capacitors are connected for realizing a continuous active filter, wherein at least one of the transconductor gain stages is an integrated gain-cell differential transconductor having an overall transconductance, $G_m$, which is relatively unchanged by process variation, comprising:

a fixed transconductor having at least one internal load current $I_1$ and characterized by a transconductance determined by the reciprocal of the magnitude of a linearizing resistance $R_{G1}$;

a translinear gain cell operatively coupled to the output of the fixed transconductor and having at least one internal load current $I_2$, the gain multiple of the translinear gain cell being determined by $I_2/I_1$ and the overall transconductance $G_m$ of the integrated gain-cell transconductor being $1/R_{G1}*I_2/I_1$; and a variable bias circuit operatively coupled to the fixed transconductor to apply a bias current $I_1$ thereto, the magnitude of $I_1$ varying in inverse proportion to variations in the resistance of a resistor $R_{G2}$ which is a resistor formed to replicate $R_{G1}$, thereby compensating transconductance $G_m$ for variations in $R_{G1}$.

16. An implantable medical device comprising:

an excitation source coupled to at least a first electrode and a second electrode, the excitation source producing current pulses of constant current flowing between the first electrode and the second electrode, the pulses sent in bursts at a burst frequency and having a pulse frequency at which the pulses are repeated;

a first high pass filter filtering voltage signals received by at least a third electrode and a fourth electrode to produce filtered voltage signals;

a first bandpass filter coupled to the amplifier and having a center frequency of approximately the pulse frequency;

a rectifier coupled to the first bandpass filter and rectifying the filtered and amplified voltage signals to produce rectified signals;

an integrator coupled to the rectifier and integrating the rectified signals to produce integrated signals;

a sample-and-hold coupled to the integrator and sampling and holding the integrated signals to produce a plurality of samples; and a second bandpass filter coupled to the integrator and including an upper band cutoff frequency which is less than the burst frequency, the second bandpass filter filtering the plurality of samples to produce an output signal related to a time-varying impedance of a load and wherein the second bandpass filter has a plurality of transconductor gain cells, a plurality of capacitors connected to the outputs of at least some of the plurality of gain cells, and where the gain cells and the capacitors are connected for realizing the bandpass filter, wherein at least one of the transconductor gain stages is an integrated gain-cell differential transconductor having an overall transconductance, $G_m$, which is relatively unchanged by process variation, the differential transconductor comprising:

a fixed transconductor having at least one internal load current $I_1$ and characterized by a transconductance determined by the reciprocal of the magnitude of a linearizing resistance $R_{G1}$;

a translinear gain cell operatively coupled to the output of the fixed transconductor and having at least one internal load current $I_2$, the gain multiple of the translinear gain cell being determined by $I_2/I_1$ and the overall transconductance $G_m$ of the integrated gain-cell transconductor being $1/R_{G1}*I_2/I_1$; and a variable bias circuit operatively coupled to the fixed transconductor to apply a bias current $I_1$ thereto, the magnitude of varying in inverse proportion to variations in the resistance of a resistor $R_{G2}$ which is a resistor formed to replicate $R_{G1}$, thereby compensating transconductance $G_m$ for variations in $R_{G1}$.

17. A method of compensating an integrated gain-cell differential transconductor having an overall transconductance, $G_m$, comprising:

amplifying an input signal with a fixed transconductor having at least one internal load current $I_1$ and characterized by a transconductance proportional to the reciprocal of the magnitude of a first internal resistor having a resistance $R_{G1}$;

amplifying the output of the transconductor with a translinear gain cell operatively coupled to the output of the fixed transconductor, the transconductor having at least one internal load currents $I_2$, the gain of the translinear gain cell proportional to $I_2/I_1$ and the overall transconductance $G_m$ of the integrated gain-cell transconductor being proportional to $1/R_{G1}*I_2/I_1$; and varying the output bias current of bias current supply operatively coupled to the fixed transconductor for applying the current $I_1$ thereto by producing a control signal from a second resistor $R_{G2}$ having resistance characteristics replicating those of $R_{G1}$, the control signal operatively coupled to the fixed transconductor for varying the load current $I_1$ of the fixed transconductor in inverse proportion to the variation of $R_{G2}$, thereby compensating $G_m$ for variations in $R_{G1}$.

18. The method of claim 17 wherein the step of varying the first internal resistance comprises at least two separate resistors.

19. The method in claim 17 wherein the resistors making up $R_{G1}$ and $R_{G2}$ are laid out on an integrated circuit substrate intermediately adjacent to each other.

* * * * *